United States Patent [19]

Aliverti et al.

[11] Patent Number: 5,183,802
[45] Date of Patent: Feb. 2, 1993

[54] PHARMACEUTICAL COMPOSITIONS FOR INTRANASAL ADMINISTRATION OF CALCITONIN

[75] Inventors: Valerio Aliverti, Castellanza; Luciano Dorigotti, Basiglio; Teodoro Fonio, Arese; Mario Pinza, Corsico, all of Italy

[73] Assignee: ISF Societa per Azioni, Italy

[21] Appl. No.: 270,905

[22] Filed: Nov. 14, 1988

[30] Foreign Application Priority Data

Nov. 13, 1987 [IT] Italy ................................ 22647 A/87
Feb. 25, 1988 [IT] Italy ................................ 19541 A/88

[51] Int. Cl.$^5$ .......................................... A61K 37/30
[52] U.S. Cl. ........................................ 514/2; 514/21; 514/53; 514/572; 514/946
[58] Field of Search .................... 514/2, 21, 53, 572, 514/946

[56] References Cited

U.S. PATENT DOCUMENTS

| | | | |
|---|---|---|---|
| 3,988,309 | 10/1976 | Matsuda et al. | 530/307 |
| 4,294,829 | 10/1981 | Suzuki et al. | 514/174 |
| 4,304,692 | 12/1981 | Hughes et al. | 525/54.11 |
| 4,393,200 | 7/1983 | Miyashita et al. | 536/18.1 |
| 4,476,116 | 10/1984 | Anik | 514/15 |
| 4,548,922 | 10/1985 | Carey et al. | 514/4 |
| 4,597,900 | 7/1986 | Arlowski et al. | 530/307 |

FOREIGN PATENT DOCUMENTS

| | | |
|---|---|---|
| 37943B | 10/1981 | European Pat. Off. . |
| 94157 | 11/1983 | European Pat. Off. . |
| 127535 | 5/1984 | European Pat. Off. . |
| 115627A | 8/1984 | European Pat. Off. . |
| 122036 | 10/1984 | European Pat. Off. . |
| 173990 | 3/1986 | European Pat. Off. . |
| 183527 | 6/1986 | European Pat. Off. . |
| 187433 | 7/1986 | European Pat. Off. . |
| 214898 | 3/1987 | European Pat. Off. . |
| 215697 | 3/1987 | European Pat. Off. . |
| 272097 | 6/1988 | European Pat. Off. . |
| 275457 | 7/1988 | European Pat. Off. . |
| 285367 | 10/1988 | European Pat. Off. . |
| 61-126034 | 6/1986 | Japan . |
| 1354535 | 5/1974 | United Kingdom . |
| 1490079 | 10/1977 | United Kingdom . |
| 1516947 | 7/1978 | United Kingdom . |
| 2008403 | 6/1979 | United Kingdom . |
| 2042888 | 10/1980 | United Kingdom . |
| 2127689 | 4/1984 | United Kingdom . |
| 2167296A | 5/1986 | United Kingdom . |

OTHER PUBLICATIONS

Kondo et al. "Physiochemical properties and applications of α- & β-glycyrrhizins, natural surface active agents in licorice root extract" CA 105(14):120456, 1986.

L. Illum, *Archiv. For Pharmaci og Chemi*, vol. 94, pp. 127–135, 1987.
K. Morimoto et al., *J. Pharm. Pharmacol.*, 37, 134–136, 1985.
Derwent Abstract: 88-045809/07 of Japan 63002932A, published Jan. 7, 1988.
R. Ziegler, G. Holz, W. Steibl & F. Rave, *Acta. Endocrinol.*, Supple (215), 54–55, 1978.
Derwent Abstract 85-320779/51 of Japan 60224616A published Oct. 9, 1985.
Derwent Abstract 85-246152/40 of Japan 60–161924A, published Aug. 23, 1985.
M. Mishima, W. Wakita, M. Nakano, Presentation at International Conference dated Apr. 2, 1987.
M. Mishima, Y. Wakita, M. Nakano, M. Hirota, S, Ikei, M. Akagi—Presentation at Conference Oct. 20–21, 1986.
S. Oakada, M. Mishima, M. Nakano, S. Ikei, M. Akagi, and S. Shibata—Japanese Pharmacological Meeting, Apr. 4, 1988.
M. Mishima et al., *J. Pharmacobio-Dyn*, 10, s–69 (1987).
S. Hirai, T. Yashiki and Mima, *Int. J. Pharmaceutics* 9, 165–172 and 173–184, (1981).
S. Hirai, et al., *Diabetes*, vol. 27, No. 3, p. 296, 1978.
Derwent Abstract 82491 D/45 of Japan 56122309, published Sep. 25, 1981.
Derwent Abstract 92092D/50 of Japan 56140924, published Nov. 4, 1981.
K. Morimoto et al., *J. Pharm. Pharmacol* vol. 37, p. 759, 1985.
M. R. Gibson, Lloydia, vol. 41, No. 4, pp. 348–349 (1978).
E. Azaz & R. Segal, *Pharm. Acta. Helv.*, 55, Nr. 6, pp. 183–186 (1980).
Chem. Abs. 84 : 155579d (1976) of A. Otsuka et al., *Yakugaku Zasshi*, 96(2), 203–8, (1976).
R. Segal, E. Touitou & S. Pisanty, Fourth Int. Conf. on Pharmaceutical Technology, Jun. 1986, Paris.
R. Segal and S. Pisanty, *J. Clinical Pharmacy & Therapeutics* 12, 165–171 (1987).
Derwent Abstract : 87-104723/15 of Japan 62051604, published Mar. 6, 1987.
Derwent Abstract : 83-773656 Japan 58140014A published Aug. 19, 1983.
Derwent Abstract 82-66899E Japan 57106612A published Jul. 12, 1982.

*Primary Examiner*—Douglas W. Robinson
*Assistant Examiner*—Jean C. Witz
*Attorney, Agent, or Firm*—Dara L. Dinner; Stephen Venetianer; Edward T. Lentz

[57] ABSTRACT

Compositions for the treatment of osteoporosis and related diseases comprise calcitonin and, as an absorption enhancer, a glycyrrhizinate.

22 Claims, No Drawings

PHARMACEUTICAL COMPOSITIONS FOR INTRANASAL ADMINISTRATION OF CALCITONIN

The present invention relates to novel pharmaceutical compositions containing calcitonins, and to a novel method of enhancing the absorption of a calcitonin across a mucosal membrane.

The calcitonins are a class of pharmacologically active peptides, of both natural and synthetic origin, which contain approximately thirty two amino acids, and which have the ability to regulate serum calcium levels.

Various calcitonins, including e.g. natural human, salmon and eel calcitonins and the synthetic eel calcitonin analogue elcatonin are now commercially available and commonly employed, e.g. in the treatment of Paget's disease, Sudeck's disease and osteoporosis.

A considerable and well known problem with the administration of peptides is that they are susceptible to rapid acid- and enzyme-induced degradation when administered orally. For this reason, parenteral administration has been, hitherto, the most widely used means of administration and, in the case of peptides of higher molecular weight, such as the calcitonins, has been the only significant effective means of administration.

It is widely recognised that administration by injection can be both inconvenient and unpleasant for the patient, particularly when the administration has to be repeated at regular intervals for long periods, e.g. in the treatment of post-menopausal osteoporosis with calcitonins. Thus, there has been growing interest in the administration of peptides by more acceptable non-invasive alternative routes, for example in the form of sublingual tablets, suppositories, intrapulmonary powders, intranasal drops, sprays, powders, gels, ointments and inserts (see for example EP 94157 (Takeda), EP 173990 (Teijin , U.S. Pat. No. 4,476,116 (Syntex) and GB 2,042,888 (Teijin)).

A significant problem with many peptides, particularly those of higher molecular weights, is that they are only poorly absorbed across biological membranes, e.g. mucosal membranes, and thus the bioavailability of the peptide is often very low. Considerable research has therefore been carried out in order to find methods of improving the trans-epithelial absorption of peptides. One approach is to use an adjuvant or absorption enhancer and there are numerous published reports of compounds which are claimed to have peptide absorption-enhancing properties.

Thus, for example, choline esters (EP 214898), acyl carnitines (EP 215697), aldoses and glucosamines (Japanese Pat. Appl. No. 61 126034), ascorbates and salicylates (EP 37943), alpha-cyclodextrin (EP 0094157), pyroglutamate esters (EP 173990), chelating agents (U.S. Pat. No. 4,476,116) and various other compounds (EP 183527) have been proposed as absorption enhancers.

Recently it has also been proposed (Morimoto et al., *Int. J. Pharm.* 37, 134-136, 1985) that an aqueous polyacrylic acid gel base could improve the absorption of a calcitonin, elcatonin, through the nasal mucosa.

It has also been reported that a component of liquorice, sodium glycyrrhetinate, can enhance the nasal absorption of insulin (Mishima et al., *J. Pharmacobio-Dyn.*, 10, s-69 (1987). However, the authors of the report demonstrated that sodium glycyrrhetinate is weaker than sodium caprate as an absorption-enhancing agent for insulin.

There are many published reports that surfactants can enhance the absorption of polypeptides, see for example EP 115627 (Armour), GB 2,127,689 (Sandoz), U.S. Pat. No. 4,548,922 (Carey et al) and Hirai et al., *Int. J. Pharm.*, 9, 165-184, 1981.

However, a recognised problem with surfactant absorption promoters is that they can cause irritation and histolesion at the site of administration. In the case of nasal administration, it has been proposed (see Hirai et al. supra) that the ability of a surfactant to enhance absorption arises at least in part from its ability to cause perturbation or disorder of the structural integrity of the nasal mucosa; i.e. the irritation and histolesive activity of the surfactant are directly linked to its ability to enhance absorption.

The problems of irritation, histolesion and, consequently, poor patient tolerability become of great importance when the peptide is administered regularly over a prolonged period.

It is evident, from the high level of continuing research into methods of improving the absorption of peptides, that there remains a need for compositions containing peptides such as calcitonins, which can be administered by a route other than the parenteral route, which give rise to adequate blood levels of the peptide, i.e. have good bioavailability, and, importantly, are well tolerated by the patient over a prolonged period.

It has now been found that the 3-(2-O-$\beta$-D-glucopyranuronosyl-alpha-D-glucopyranosiduronic acid) derivative of glycyrrhetinic acid, known as glycyrrhizinic acid, and its salts not only have excellent mucosal membrane absorption-promoting properties with regard to calcitonin, but, moreover, do not give rise to the above-mentioned local toxicity problems associated with many absorption promoters when administered over a prolonged period.

In a first aspect, therefore, the present invention provides a method of enhancing the absorption of a calcitonin across a mucosal membrane, which method comprises co-administering with the calcitonin an effective amount of an absorption enhancer which is a glycyrrhizinate.

The present invention also provides a pharmaceutical composition comprising a calcitonin; an effective amount of an absorption enhancer which is a glycyrrhizinate and a pharmaceutically acceptable carrier.

In addition to the physiological tolerability of the compositions of the present invention, a further advantage is that glycyrrhizinates have been found to be more effective nasal absorption enhancers than known agents such as benzalkonium chloride and sodium taurocholate.

The term glycyrrhizinate as used herein is intended to mean both glycyrrhizinic acid and its carboxylate salts. Particular glycyrrhizinate salts are ammonium glycyrrhizinate and the alkali metal salts e.g. sodium glycyrrhizinate and potassium glycyrrhizinate. A preferred salt is ammonium glycyrrhizinate.

The term calcitonin as used herein is intended to refer to that class of pharmacologically active polypeptides including not only naturally occurring calcitonins but also various derivatives and analogues thereof, e.g. in which one or more of the amino acid residues or sequences naturally present is omitted, replaced, reversed or otherwise derivatised or in which the N- or C- terminal is modified.

The general term calcitonin, as used hereinafter, is intended to mean all such calcitonins whether naturally occurring or synthetic.

Examples of naturally occurring calcitonins include: human calcitonin, Chemical Abstract Service Registry Number (CAS RN)=21215-62-3, which has the structure:

H—Cys—Gly—Asn—Leu—Ser—Thr—Cys—Met—Leu—Gly—
—Thr—Tyr—Thr—Gln—Asp—Phe—Asn—Lys—Phe—His—
—Thr—Phe—Pro—Gln—Thr—Ala—Ile—Gly—Val—Gly—
—Ala—Pro—NH$_2$;

rat calcitonin (CAS RN=11118-25-5) which has the structure:

H—Cys—Gly—Asn—Leu—Ser—Thr—Cys—Met—Leu—Gly—
—Thr—Tyr—Thr—Gln—Asp—Leu—Asn—Lys—Phe—His—
—Thr—Phe—Pro—Gln—Thr—Ser—Ile—Gly—Val—Gly—
—Ala—Pro—NH$_2$;

salmon calcitonin (CAS RN=47931-85-1) which has the structure:

H—Cys—Ser—Asn—Leu—Ser—Thr—Cys—Val—Leu—Gly—
—Lys—Leu—Ser—Gln—Glu—Leu—His—Lys—Leu—Gln—
—Thr—Tyr—Pro—Arg—Thr—Asn—Thr—Gly—Ser—Gly—
—Thr—Pro—NH$_2$;

eel calcitonin (CAS RN=57014-02-5) which has the structure:

H—Cys—Ser—Asn—Leu—Ser—Thr—Cys—Val—Leu—Gly—
—Lys—Leu—Ser—Gln—Glu—Leu—His—Lys—Leu—Gln—
—Thr—Tyr—Pro—Arg—Thr—Asp—Val—Gly—Ala—Gly—
—Thr—Pro—NH$_2$;

reduced chicken calcitonin I (CAS RN=96157-98-1) which has the structure:

H—Cys—Ala—Ser—Leu—Ser—Thr—Cys—Val—Leu—Gly—
—Lys—Leu—Ser—Gln—Glu—Leu—His—Lys—Leu—Gln—
—Thr—Tyr—Pro—Arg—Thr—Asp—Val—Gly—Ala—Gly—
—Thr—Pro—NH$_2$;

chicken calcitonin II (CAS RN=103468-65-1) which has the structure:

H—gamma—Glu—Cys—Gly—OH   H—gamma—Glu—Cys—Gly—OH
                |                              |
         H—Cys—Ala—Ser—Leu—Ser—Thr—Cys—Val—Leu—Gly—
—Lys—Leu—Ser—Gln—Glu—Leu—His—Lys—Leu—Gln—
—Thr—Tyr—Pro—Arg—Thr—Asp—Val—Gly—Ala—Gly—
—Thr—Pro—NH$_2$;

ox calcitonin (CAS RN=26112-29-8) which has the structure:

H—Cys—Ser—Asn—Leu—Ser—Thr—Cys—Val—Leu—Ser—
—Ala—Tyr—Trp—Lys—Asp—Leu—Asn—Asn—Tyr—His—
—Arg—Phe—Ser—Gly—Met—Gly—Phe—Gly—Pro—Glu—
—Thr—Pro—NH$_2$;

pig calcitonin (CAS RN=12321-44-7) which has the structure:

H—Cys—Ser—Asn—Leu—Ser—Thr—Cys—Val—Leu—Ser—
—Ala—Tyr—Trp—Arg—Asn—Leu—Asn—Asn—Phe—His—
—Arg—Phe—Ser—Gly—Met—Gly—Phe—Gly—Pro—Glu—
—Thr—Pro—NH$_2$; and sheep calcitonin (CAS RN=40988-57-6) which has the structure:

H—Cys—Ser—Asn—Leu—Ser—Thr—Cys—Val—Leu—Ser—
—Ala—Tyr—Trp—Lys—Asp—Leu—Asn—Asn—Tyr—His—
—Arg—Tyr—Ser—Gly—Met—Gly—Phe—Gly—Pro—Glu—
—Thr—Pro—NH$_2$.

Examples of calcitonins wherein one or more amino acids have been omitted are the des-[Ser$^2$, Tyr$^{22}$]-Gly$^8$-calcitonins described in U.S. Pat. No. 4,597,900 and the des-[Tyr$^{22}$]-salmon calcitonin described in U.S. Pat. No. 4,304,692.

Examples of calcitonins wherein the naturally occurring sequence has been modified include the 1,7-dicarba-calcitonins such as eel 1,7-dicarbacalcitonin (elcatonin CAS RN=60731-46-6) which has the structure:

————————(CH$_2$)$_5$————————
CO—Ser—Asn—Leu—Ser—Thr—NH—CH—CO—Val—Leu—Gly—

—Lys—Leu—Ser—Gln—Glu—Leu—His—Lys—Leu—Gln—

—Thr—Tyr—Pro—Arg—Thr—Asp—Val—Gly—Ala—Gly—

—Thr—Pro—NH$_2$;

salmon 1,7-dicarbacalcitonin (CAS RN=60864-37-1) which has the structure:

```
       ┌─────────(CH₂)₅─────────┐
CO—Ser—Asn—Leu—Ser—Thr—NH—CH—CO—Val—Leu—Gly—
```

—Lys—Leu—Ser—Gln—Glu—Leu—His—Lys—Leu—Gln—

—Thr—Tyr—Pro—Arg—Thr—Asn—Thr—Gly—Ser—Gly—

—Thr—Pro—NH$_2$; and human 1,7-dicarbacalcitonin (CAS RN=66811-56-1) which has the structure:

```
       ┌─────────(CH₂)₅─────────┐
CO—Gly—Asn—Leu—Ser—Thr—NH—CH—CO—Met—Leu—Gly—
```

—Thr—Tyr—Thr—Gln—Asp—Phe—Asn—Lys—Phe—His—

—Thr—Phe—Pro—Gln—Thr—Ala—Ile—Gly—Val—Gly—

—Ala—Pro—NH$_2$.

In the context of the present invention, a particularly preferred calcitonin is elcatonin (CAS RN=60731-46-6). The preparation and properties of elcatonin and related 1,7-dicarbacalcitonins are described in British Patent Number 1,516,947 (Toyo Jozo).

Another preferred calcitonin is naturally occurring eel calcitonin (CAS RN 57014-02-5). The preparation and properties of eel calcitonin are described in U.S. Pat. No. 3,988,309 (Matsuda et al).

The compositions of the present invention suitably can be administered by methods known in the art for transmucosal delivery of pharmacologically active substances. The compositions can be administered to, for example, the nasal, sublingual, buccal, rectal, vaginal and colonic mucosa and can take the form of drops, aerosols, tablets, capsules, powders, gels, ointments, inserts, suppositories, pessaries, patches and membranes. The compositions can also take the form of enterically coated solid oral compositions as described in, for example, EP 127535 (Hadassah Medical Organisation).

Particular compositions are those intended for administration to the nasal mucosa.

When the composition is intended for delivery to the nasal mucosa, particular dosage forms are aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container. The sealed container can take the form of a cartridge or refill for use with an atomising device, or it can take the form of a unitary dispensing device such as a single dose nasal inhaler (see French Patent Application FR 2578426) or an aerosol dispenser fitted with a metering valve and which is intended for disposal once the contents of the container have been exhausted. Where the dosage form comprises an aerosol dispenser, it will contain a propellant which can be a compressed gas such as compressed air or an organic propellant such as a fluorochlorohydrocarbon. Such aerosol dispensers are well known in the art. The aerosol dosage forms can also take the form of a pump-atomiser and such forms are also well known in the art.

The atomising or dispensing devices for dispensing aerosol sprays typically are designed to dispense particles of a size greater than 10 micrometers. In order to ensure that significant quantities of the composition remain in contact with the oral or nasal mucosa, and are not inhaled, the particles suitably are approximately 10–160 micrometers in size.

When the composition is intended to be administered as a liquid spray, the viscosity of the liquid composition will be adjusted as necessary according to known methods to ensure that the composition is sprayable.

The solvents or liquid carriers used in the present formulations are preferably aqueous but can also be chosen from the physiologically acceptable non-aqueous solvents. Examples of non-aqueous solvents or carriers are alcohols, particularly polyhydroxy alcohols such as propylene glycol and glycerol, and vegetable and mineral oils. Such non-aqueous solvents or carriers can be added in various concentrations to water to form solutions, oil-in-water emulsions and water-in-oil emulsions. The solvent preferably is water.

In addition to a solvent or carrier, the liquid formulations of the present invention can contain excipients such as antioxidants, stabilisers, preservatives, agents for adjusting viscosity and tonicity, and buffering agents.

When a preservative is employed, it is chosen such that in the quantities needed to preserve the formulation, it does not cause irritation of the nasal mucosa. This is particularly important when the formulation is intended to be administered on a long term basis, for example when used in the treatment of post-menopausal osteoporosis. Suitable preservatives are the alkyl p-hydroxybenzoates (parabens) such as methyl p-hydroxybenzoate and propyl p-hydroxybenzoate. Preferably the preservative does not comprise benzalkonium chloride.

Particular dosage forms for buccal and sublingual administration are gels, suspensions, tablets, patches, powders, ointments and solutions. Particular dosage forms for vaginal and rectal administration include pessaries, suppositories, solutions, foams, suspensions, gels, ointments and tablets.

The above-mentioned compositions can be made according to well known pharmaceutical procedures, see for example Remington's Pharmaceutical Sciences, 17th Edition, Mack Publishing Company, 1985.

When the composition is enterically coated and is intended for oral administration, typically it can take the form of a tablet or capsule coated with a coating agent which ensures passage of the calcitonin through the stomach and small intestine and its subsequent release in the colon. Suitable coating agents include anionic polymers such as acrylic acid/methacrylic acid ester copolymers (e.g. Eudragit S).

The compositions can also contain a protease inhibitor, preferably a non-surfactant protease inhibitor, for example as described in EP 127535.

The compositions of the present invention can be used in the treatment of diseases such as Paget's disease (osteitis deformans), osteoporosis, Sudeck's disease and various hypercalcaemic conditions (see, for example, the Physician's Desk Reference, 42nd Edition, 1988, pages 1796 and 1797).

The compositions will be administered to the patient in dosages which contain an amount of calcitonin effective to treat the disease in question.

The quantity of pharmacologically active substance in a unit dose of the compositions of the present invention will vary according to the potency of the calcitonin and the nature of the composition. However, in general, a unit dose of a composition intended for human use typically contains between 5 and 200 International Units (I.U.) of a calcitonin. For elcatonin, a unit dose preferably contains from 20 to 100 I.U.

The term "International Unit" refers to the appropriate International Reference Preparation (I.R.P.) of human, salmon or porcine calcitonins, or elcatonin, established by the National Institute for Biological Standards and Control, Blanche Lane, South Mimms, Potters Bar, Hertfordshire, EN6 3QG, United Kingdom.

When the formulation is a liquid formulation, particularly a spray, the volume of a unit dose typically is in the range 50 to 130 mcl.

The pH of the compositions of the present invention can vary within a broad range according to the chemico-physical properties of the different ingredients in the compositions. However, suitably the pH of the composition is in the range from pH 3 to 8, particularly from approximately pH 4.5 to approximately pH 6.

In order to maintain a particular pH value, buffering agents can be used.

Examples of buffering agents are citrates, phosphates or acetates, a particular buffering agent being a mixture of citric acid and sodium citrate.

The concentration of the glycyrrhizinate absorption enhancer typically is at least 0.1% (w/w), suitably 0.5 to 10% (w/w), and preferably 0.5 to 5% (w/w) of the total weight of the composition.

Where the composition is a liquid or gel composition, the glycyrrhizinate suitably is present in an amount corresponding to between 0.5 g and 5 g per 100ml of composition. Preferably the glycyrrhizinate is present in an amount corresponding to approximately 2 g/100 ml.

For aqueous compositions, the final pharmaceutical form, i.e. liquid solution or gel, will depend upon the pH, the ionic strength of the solution and the concentration of glycyrrhizinate. In general, compositions having a pH of about 5.5 and above will exist as liquids whilst compositions having a lower pH value will tend to be more viscous and, at around pH 4.5, will exist in a gel form.

The invention will now be illustrated in greater detail by the following examples.

EXAMPLES 1-9

TABLE 1

|  | Example No. | | | | | | | | |
| --- | --- | --- | --- | --- | --- | --- | --- | --- | --- |
|  | 1 | 2 | 3 | 4 | 5 | 6 | 7 | 8 | 9 |
| Elcatonin (mcg) (6500 I.U./mg potency) | 1415 | 1415 | 1415 | 7380 | 7380 | 1415 | 7380 | 1415 | 7380 |
| Ammonium Glycyrrhizinate (g) | 1 | 2 | 5 | 1 | 5 | 2 | 2 | 0.5 | 0.5 |
| Citric Acid (mg) | 37 | 37 | 37 | 37 | 37 | 37 | 37 | 37 | 37 |
| Sodium citrate dihydrate (mg) | 463 | 463 | 463 | 463 | 463 | 463 | 463 | 463 | 463 |
| Methyl p-hydroxybenzoate (mg) | 130 | 130 | 130 | 130 | 130 | — | — | 130 | 130 |
| Propyl p-hydroxybenzoate (mg) | 20 | 20 | 20 | 20 | 20 | — | — | 20 | 20 |
| Distilled water | q.s to 100 ml | | | | | | | | |
| 1N NaOH (q.s to pH-) | 6 | 6 | 6 | 6 | 6 | 6 | 6 | 4.5* | 4.5* |

*0.1N NaOH used to adjust pH to 4.5

The formulations of Examples 1 to 9 were prepared by mixing together the ammonium glycyrrhizinate, citric acid, sodium citrate dihydrate, methyl p-hydroxybenzoate, propyl p-hydroxybenzoate, distilled water and sodium hydroxide in a water bath regulated at a temperature of about 60° C. The resulting solution was allowed to cool to room temperature and the elcatonin was then added.

The formulations of Examples 8 and 9 are gels.

EXAMPLE 10

1415 mcg of elcatonin (6500 I.U./mg potency) were exactly weighed and dissolved with 100 ml of a vehicle made up with the following ingredients:
ammonium glycyrrhizinate, as absorption enhancer, 1 g;
acetic acid 200 mg and sodium acetate trihydrate 200 mg, as buffering ingredients;
methyl p-hydroxybenzoate 130 mg and propyl p-hydroxybenzoate 20 mg, as preservative agents;
distilled water q.s. to 100 ml;
the pH of the vehicle was adjusted to 3.5 by addition of HCl 1N.

The preparation of the vehicle is carried out in a water bath regulated at a temperature of about 60° C. The gel obtained is then allowed to cool to room temperature before addition of the active ingredient.

EXAMPLE 11

1670 mcg of salmon calcitonin (5500 I.U./mg potency) were exactly weighed and dissolved with 100 ml of a vehicle made up with the following ingredients:
ammonium glycyrrhizinate, as absorption enhancer, 2 g;
citric acid 37 mg and sodium citrate dihydrate 463 mg, as buffering ingredients;
methyl p-hydroxybenzoate 130 mg and propyl p-hydroxybenzoate 20 mg, as preservative agents;
distilled water q.s. to 100 ml;
the pH of the vehicle was adjusted to 6 by addition of NaOH 1N.

The preparation of the vehicle is carried out in a water bath regulated at a temperature of about 60° C. The obtained solution is then allowed to cool to room temperature before addition of the active ingredient.

EXAMPLE 12

1840 mcg of eel-calcitonin (5000 I.U./mg potency) were exactly weighed and dissolved with 100 ml of a vehicle made up with the following ingredients:
ammonium glycyrrhizinate, as absorption enhancer, 2 g;
citric acid 37 mg and sodium citrate dihydrate 463 mg, as buffering ingredients;
methyl p-hydroxybenzoate 130 mg and propyl p-hydroxybenzoate 20 mg, as preservative agents;
distilled water q.s. to 100 ml;
the pH of the vehicle was adjusted to 6 by addition of NaOH 1N.

The preparation of the vehicle is carried out in a water bath regulated at a temperature of about 60° C. The obtained solution is then allowed to cool to room temperature before addition of the active ingredient.

EXAMPLES 13 AND 14

The following compositions were prepared according to the method described in Examples 1 to 9.

TABLE 2

| | Example No. | |
|---|---|---|
| | 13 | 14 |
| Elcatonin (mcg) (6500 I.U./mg potency) | 7380 | 3690 |
| Ammonium Glycyrrhizinate (g) | 2 | 2 |
| Citric Acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Distilled water | q.s. to 100 ml | |
| 1N NaOH | q.s. to pH 6 | |

EXAMPLE 15

Trial A

The preparation reported in Example 2 containing ammonium glycyrrhizinate 2% as absorption enhancer, was compared, on a test of pharmacodynamic activity i.e. lowering of calcium concentration in the serum, with the following preparations:
a formulation containing the same concentration of elcatonin and the same excipients with the exception of the ammonium glycyrrhizinate (reference preparation A); a formulation containing the same concentration of elcatonin, benzalkonium chloride 0.01% and citrates as excipients (reference preparation B); a formulation containing the same concentration of elcatonin, sodium taurocholate 1%, parabens 0.15% and citrates (reference Preparation C).

The preparations were administered intranasally with a small catheter, in the volume of 10 mcl, to groups of 10 male Sprague Dawley rats weighing 160±10 g. The animals, fasted overnight, were anaesthetized with tribromoethanol (TBE) 2% (0.9 ml/100 g b.w. given i.p. 15 min before receiving elcatonin.

Serum calcium concentration was measured (with an atomic absorption spectrophotometer VARIAN 30/40) on blood samples obtained in each animal, from the orbital sinus, 60 and 120 min after administration of the product. Basal values were obtained at the same times in animals fasted and anaesthetized as described above but receiving no treatment.

The results are reported in Table 3.

TABLE 3

| | Administered dosage | Percent decrease of serum calcium as compared with basal values | |
|---|---|---|---|
| | I.U./kg | 1 h | 2 h |
| Preparation of this invention - Reported in example 2 | 4 | 18.1 | 21.3 |
| Reference preparation A | 4 | 12.8 | 4.5 |
| Reference preparation B | 4 | 14.1 | 5.2 |
| Reference preparation C | 4 | 15.5 | 15.8 |

Trial B

The preparation reported in Example 1 containing ammonium glycyrrhizinate 1% as absorption enhancer, was compared, on a test of pharmacodynamic activity i.e. lowering of calcium concentration in the serum, with the following preparations:
a formulation containing the same concentration of elcatonin and the same excipients with the exception of the ammonium glycyrrhizinate (reference preparation A); a formulation containing the same concentration of elcatonin, benzalkonium chloride 0.01% and citrates as excipients (reference preparation B).

The testing methodologies were the same described for Trial A.

The results are reported in Table 4.

TABLE 4

| | Administered dosage | Percent decrease of serum calcium as compared with basal values | |
|---|---|---|---|
| | I.U./kg | 1 h | 2 h |
| Preparation of this invention - Reported in example 1 | 4 | 15.6 | 13.3 |
| Reference preparation A | 4 | 12.0 | 3.6 |
| Reference preparation B | 4 | 13.5 | 2.3 |

Trial C

The preparation reported in Example 3 containing ammonium glycyrrhizinate 5% as absorption enhancer, was compared, on a test of pharmacodynamic activity i.e. lowering of calcium concentration in the serum, with the following preparations:

a formulation containing the same concentration of elcatonin and the same excipients with the exception of the ammonium glycyrrhizinate (reference preparation A); a formulation containing the same concentration of elcatonin, benzalkonium chloride 0.01% and citrates as excipients (reference preparation B); a formulation containing the same concentration of elcatonin, sodium taurocholate 1%, parabens 0.15% and citrates (reference preparation C).

The testing methodologies were the same described for Trial A except for the fact that blood samples were obtained 60, 120 and 240 min after treatment. The results are reported in Table 5.

TABLE 5

|  | Administered dosage I.U./kg | Percent decrease of serum calcium as compared with basal values | | |
|---|---|---|---|---|
|  |  | 1 h | 2 h | 4 h |
| Preparation of this invention - Reported in example 3 | 4 | 18.4 | 21.9 | 9.0 |
| Reference preparation A | 4 | 10.4 | 3.5 | −0.5 |
| Reference preparation B | 4 | 12.1 | 5.2 | 0.7 |
| Reference preparation C | 4 | 14.2 | 20.4 | 2.2 |

EXAMPLE 16

Trial D

The preparation reported in Example 13, containing elcatonin as active ingredient and ammonium glycyrrhizinate 2% as absorption enhancer, was compared on a test of bioavailability (i.e. kinetics of elcatonin in the serum) with the following preparations:
a formulation containing the same concentration of elcatonin and the same excipients with the exception of the ammonium glycyrrhizinate (reference preparation A); a formulation containing the same concentration of elcatonin, benzalkonium chloride 0.01% and citrates as excipients (reference preparation B).

The preparations were administered intranasally (with a metered pump releasing a volume of 100 mcl) to two male Beagle dogs weighing 10 kg. Each animal received one puff in each nostril, i.e. a total of 80 I.U. Elcatonin concentration in the serum was measured by RIA on blood samples obtained in each animal, (from the saphenous vein) at 5 min intervals after administration of the product (from time 0 up to 60 min). The results are reported in Table 6.

TABLE 6

|  | Administered dosage I.U./kg | Elcatonin peak concentrations and AUC values | | |
|---|---|---|---|---|
|  |  | Peak concentration pg/ml | Peak time min | AUC min × pg/ml |
| Preparation of this invention - Reported in example 13 | 8 | 515 | 10 | 7587 |
| Reference preparation A | 8 | 95 | 10 | 1270 |
| Reference preparation B | 8 | 217 | 20 | 2869 |

EXAMPLES 17, 18 AND 19

The following compositions were prepared according to the method described in Examples 1 to 9.

TABLE 7

|  | Example No. | | |
|---|---|---|---|
|  | 17 | 18 | 19 |
| Elcatonin (mcg) (6500 I.U./mg potency) | 7380 | 3690 | 3690 |
| Ammonium Glycyrrhizinate (g) | 0.5 | 0.5 | 1 |
| Citric Acid (mg) | 37 | 37 | 37 |
| Sodium citrate dihydrate (mg) | 463 | 463 | 463 |
| Methyl p-hydroxybenzoate (mg) | 130 | 130 | 130 |
| Propyl p-hydroxybenzoate (mg) | 20 | 20 | 20 |
| Distilled water | q.s. to 100 ml | | |
| 1N NaOH | q.s. to pH 6 | | |

EXAMPLES 20-25

TABLE 8

|  | Example No. | | | | | |
|---|---|---|---|---|---|---|
|  | 20 | 21 | 22 | 23 | 24 | 25 |
| Elcatonin (mcg) (6500 I.U./mg potency) | 7380 | 3690 | 7380 | 3690 | 7380 | 3690 |
| Ammonium glycyrrhizinate (g) | 0.5 | 0.5 | 1 | 1 | 2 | 2 |
| Citric acid (mg) | 37 | 37 | 37 | 37 | 37 | 37 |
| Sodium citrate dihydrate (mg) | 463 | 463 | 463 | 463 | 463 | 463 |
| Methyl p-hydroxybenzoate (mg) | 130 | 130 | 130 | 130 | 130 | 130 |
| Propyl p-hydroxybenzoate (mg) | 20 | 20 | 20 | 20 | 20 | 20 |
| Sodium chloride (mg) | 600 | 600 | 600 | 600 | 600 | 600 |
| Polysorbate 80 (mg) | 5 | 5 | 5 | 5 | 5 | 5 |
| Distilled water | q.s. to 100 ml | | | | | |
| 1N NaOH | q.s. to pH 6 | | | | | |

The formulations of Examples 20 to 25 were prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution was allowed to cool to room temperature and the elcatonin was then added.

EXAMPLES 26-31

TABLE 9

|  | Example No. | | | | | |
|---|---|---|---|---|---|---|
|  | 26 | 27 | 28 | 29 | 30 | 31 |
| Elcatonin (mcg) (6500 I.U./mg potency) | 7380 | 3690 | 7380 | 3690 | 7380 | 3690 |
| Ammonium glycyrrhizinate (g) | 0.5 | 0.5 | 1 | 1 | 2 | 2 |
| Citric acid (mg) | 37 | 37 | 37 | 37 | 37 | 37 |
| Sodium citrate dihydrate (mg) | 463 | 463 | 463 | 463 | 463 | 463 |
| Methyl p-hydroxybenzoate (mg) | 130 | 130 | 130 | 130 | 130 | 130 |
| Propyl p-hydroxybenzoate (mg) | 20 | 20 | 20 | 20 | 20 | 20 |
| Sodium chloride (mg) | 600 | 600 | 600 | 600 | 600 | 600 |
| Polysorbate 80 (mg) | 10 | 10 | 10 | 10 | 10 | 10 |
| Distilled water | q.s. to 100 ml | | | | | |
| 1N NaOH | q.s. to pH 6 | | | | | |

The formulations of Examples 26 to 31 were prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution was allowed to cool to room temperature and the elcatonin was then added.

EXAMPLES 32-37

TABLE 10

| | Example No. | | | | | |
|---|---|---|---|---|---|---|
| | 32 | 33 | 34 | 35 | 36 | 37 |
| Elcatonin (mcg) (6500 I.U./mg potency) | 7380 | 3690 | 7380 | 3690 | 7380 | 3690 |
| Ammonium glycyrrhizinate (g) | 0.5 | 0.5 | 1 | 1 | 2 | 2 |
| Citric acid (mg) | 37 | 37 | 37 | 37 | 37 | 37 |
| Sodium citrate dihydrate (mg) | 463 | 463 | 463 | 463 | 463 | 463 |
| Methyl p-hydroxybenzoate (mg) | 130 | 130 | 130 | 130 | 130 | 130 |
| Propyl p-hydroxybenzoate (mg) | 20 | 20 | 20 | 20 | 20 | 20 |
| Sodium chloride (mg) | 600 | 600 | 600 | 600 | 600 | 600 |
| Distilled water | q.s. to 100 ml | | | | | |
| 1N NaOH | q.s. to pH 6 | | | | | |

The formulations of Examples 32 to 37 were prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution was allowed to cool to room temperature and the elcatonin was then added.

EXAMPLE 38

Trial E

The preparations reported in Examples 36 and 37, containing elcatonin as active ingredient (respectively 40 I.U./100 mcl and 20 I.U./100 mcl) and ammonium glycyrrhizinate 2% as absorption enhancer, were compared on a test of bioavailability (i.e. kinetics of elcatonin in the serum) with the following preparations: a formulation containing the same concentration of elcatonin of Example 36 and the same excipients with the exception of the ammonium glycyrrhizinate (reference preparation A); a formulation containing the same concentration of elcatonin of Example 37 and the same excipients with the exception of the ammonium glycyrrhizinate (reference preparation B); a formulation containing 40 I.U./ml of elcatonin in isoosmotic acetate buffer, pH 4.25 (reference preparation C).

The preparations of Examples 36 and 37 and the reference preparations A and B were administered intranasally (with a metered pump releasing a volume of 100 mcl) to six male volunteers. Each volunteer received one puff in each nostril, i.e. a total of 80 I.U. for the preparation of Example 36 and for the reference preparation A or 40 I.U. for the preparation of Example 37 and for the reference preparation B.

The reference preparation C was administered intramuscularly in a volume of 1 ml (40 I.U.) to the same six subjects with a cross-over design. Elcatonin concentration in the serum was measured by radio immunoassay (RIA) of blood samples obtained from each subject at 5 minute intervals after administration of the product (from time 0 up to 60 minutes).

The results are reported in Table 11.

TABLE 11

| | | Elcatonin mean peak concentrations and AUC values | | |
|---|---|---|---|---|
| | Administered dose I.U. | Peak concentration pg/ml | Peak time min | AUC (Mean Standard Error) min × pg/ml |
| Composition of example 36 | 80 | 186.3 | 15.2 | 3551.2 (±160.1) |
| Composition of example 37 | 40 | 92.5 | 15.1 | 2301.9 (±170.7) |
| Reference preparation A | 80 | 57.6 | 15.6 | 1270.2 (±135.6) |
| Reference preparation B | 40 | 27.9 | 15.1 | 551.0 (±85.4) |
| Reference preparation C | 40 | 233.3 | 20.6 | 3675.2 (+190.6) |

EXAMPLES 39 AND 40

TABLE 12

| | Example No. | |
|---|---|---|
| | 39 | 40 |
| Salmon calcitonin (mcg) (5500 I.U./mg potency) | 9090 | 18180 |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 39 and 40 were prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution was allowed to cool to room temperature and the salmon calcitonin was then added.

EXAMPLES 41 AND 42

TABLE 13

| | Example No. | |
|---|---|---|
| | 41 | 42 |
| Eel calcitonin (mcg) (5000 I.U./mg potency) | 10000 | 20000 |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 41 and 42 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the eel calcitonin is then added.

EXAMPLES 43 AND 44
TABLE 14

|  | Example No. | |
| --- | --- | --- |
|  | 43 | 44 |
| Chicken calcitonin II (mcg) | 10000 | 20000 |
| (5000 I.U./mg potency) | | |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 43 and 44 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the chicken calcitonin II is then added.

EXAMPLES 45 AND 46
TABLE 15

|  | Example No. | |
| --- | --- | --- |
|  | 45 | 46 |
| Human calcitonin (mg) | 250 | 500 |
| (200 I.U./mg potency) | | |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 45 and 46 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the human calcitonin is then added.

EXAMPLES 47 AND 48
TABLE 16

|  | Example No. | |
| --- | --- | --- |
|  | 47 | 48 |
| Pig calcitonin (mg) | 834 | 1668 |
| (60 I.U./mg potency) | | |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 47 and 48 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the pig calcitonin is then added.

Powder for nasal administration

EXAMPLES 49 AND 50
TABLE 17

|  | Example No. | |
| --- | --- | --- |
|  | 49 | 50 |
| Elcatonin (mg) | 3.69 | 7.38 |
| (6500 I.U./mg potency) | | |
| Ammonium glycyrrhizinate (g) | 2.0 | 2.0 |
| Lactose q.s. to (g) | 25.0 | 25.0 |

The formulations of Examples 49 and 50 are prepared by wetting the lactose with an aqueous solution of elcatonin and drying under vacuum. The dried powder is mixed with ammonium glycyrrhizinate and the final mixture is placed into hard gelatine capsules (25 mg each capsule).

The powder is administered, after having pierced the capsules, using a nasal insufflator.

Sublingual tablets

EXAMPLES 51 AND 52
TABLE 18

|  | Example No. | |
| --- | --- | --- |
|  | 51 | 52 |
| Elcatonin (mg) | 7.7 | 15.4 |
| (6500 I.U./mg potency) | | |
| Ammonium glycyrrhizinate (g) | 4.0 | 4.0 |
| Sucrose (g) | 35.0 | 35.0 |
| Mannitol (g) | 35.0 | 35.0 |
| Polyethylene glycol 6000 (g) | 10.0 | 10.0 |
| Lactose q.s. to (g) | 120.0 | 120.0 |

The formulations of Examples 51 and 52 were prepared by mixing together the sucrose, the mannitol and the lactose. The resulting mixture was wetted with an aqueous solution of elcatonin, granulated through a stainless steel screen and dried under vacuum. The dried granules were mixed with polyethylene glycol and ammonium glycyrrhizinate and then compressed into tablets of 120 mg each.

Buccal tablets

EXAMPLES 53 AND 54
TABLE 19

|  | Example No. | |
| --- | --- | --- |
|  | 53 | 54 |
| Elcatonin (mg) | 7.7 | 15.4 |
| (6500 I.U./mg potency) | | |
| Ammonium glycyrrhizinate (g) | 4.0 | 4.0 |
| Sucrose (g) | 30.0 | 30.0 |
| Mannitol (g) | 35.0 | 35.0 |
| Polyethylene glycol 6000 (g) | 15.0 | 15.0 |
| Carbopol 934 (g) | 15.0 | 15.0 |
| Lactose q.s. to (g) | 150.0 | 150.0 |

The formulations of Examples 53 and 54 are prepared by mixing together the sucrose, the mannitol and the lactose. The resulting mixture is wetted with an aqueous solution of elcatonin, granulated through a stainless steel screen and dried under vacuum. The dried granules are mixed with ammonium glycyrrhizinate, carbopol and polyethylene glycol and then compressed into tablets of 150 mg each.

Oral tablets for colonic delivery

EXAMPLES 55 AND 56

TABLE 20

|  | Example No. | |
| --- | --- | --- |
|  | 55 | 56 |
| Elcatonin (mg) (6500 I.U./mg potency) | 15.4 | 30.8 |
| Ammonium glycyrrhizinate (g) | 6.0 | 6.0 |
| Pregelatinized starch (g) | 80.0 | 80.0 |
| Magnesium stearate (g) | 2.0 | 2.0 |
| Lactose q.s. to (g) | 210.0 | 210.0 |
| Eudragit S (g) | 20.0 | 20.0 |
| Polyethylene glycol 6000 (g) | 2.0 | 2.0 |

The formulations of Examples 55 and 56 are prepared by mixing together pregelatinized starch and the lactose. The resulting mixture is wetted with an aqueous solution of elcatonin, granulated through a stainless steel screen and dried under vacuum. The dried granules are mixed with ammonium glycyrrhizinate and magnesium stearate and then compressed into tablets of 210 mg each.

The tablets are coated with an aqueous suspension of polyethylene glycol and Eudragit, to a final weight of 232 mg/tablet.

Vaginal tablets

EXAMPLES 57 AND 58

TABLE 21

|  | Example No. | |
| --- | --- | --- |
|  | 57 | 58 |
| Elcatonin (mg) (6500 I.U./mg potency) | 15.4 | 30.8 |
| Ammonium glycyrrhizinate (g) | 8.0 | 8.0 |
| Corn starch (g) | 180.0 | 180.0 |
| Adipic acid (g) | 140.0 | 140.0 |
| Sodium bicarbonate (g) | 110.0 | 110.0 |
| Magnesium stearate (g) | 20.0 | 20.0 |
| Lactose q.s. to (g) | 1600.0 | 1600.0 |

The formulations of Examples 57 and 58 are prepared by mixing together the ammonium glycyrrhizinate, the corn starch, the adipic acid and the lactose. The resulting mixture is wetted with an aqueous solution of elcatonin, granulated through a stainless steel screen and dried under vacuum. The dried granules are mixed with sodium bicarbonate and magnesium stearate and then compressed into tablets of 1.6 g each.

We claim:

1. A pharmaceutical composition comprising a non-toxic, therapeutically effective amount of a calcitonin, a non-toxic effective amount of an absorption enhancer which is a glycyrrhizinate, and a pharmaceutically acceptable carrier.

2. The composition according to claim 1 wherein the glycyrrhizinate is ammonium glycyrrhizinate.

3. The composition according to claim 1 wherein the glycyrrhizinate is present in a concentration corresponding to at least 0.1% (w/w) of the total weight of the composition.

4. The composition according to claim 3 wherein the concentration of glycyrrhizinate is 0.5 to 5% (w/w).

5. The composition according to claim 1 wherein the calcitonin is elcatonin.

6. The composition according to claim 1 wherein the calcitonin is eel calcitonin.

7. The composition according to claim 1 in the form of a liquid or gel suitable for application to the nasal mucosa.

8. The composition according to claim 7 wherein the glycyrrhizinate is present in an amount corresponding to approximately 2 g per 100 ml of composition.

9. The composition according to claim 1 which is packaged for administration as a spray.

10. The composition according to claim 8 which is packaged for administration as a spray.

11. The composition according to claim 1 which has a pH in the range from approximately 4.5 to approximately 6.

12. The composition according to claim 1 wherein the calcitonin is elcatonin and the glycyrrhizinate is ammonium glycyrrhizinate.

13. The composition according to claim 12 in the form of a liquid suitable for application to the nasal mucosa.

14. The composition according to claim 13 which has a pH in the range from approximately 4.5 to approximately 6 and is packaged for administration as a spray.

15. The composition according to claim 14 wherein the glycyrrhizinate is present in an amount corresponding to approximately 2 g per 100ml of composition.

16. The composition according to claim 1 wherein the calcitonin is eel calcitonin and the glycyrrhizinate is ammonium glycyrrhizinate.

17. The composition according to claim 16 in the form of a liquid suitable for application to the nasal mucosa.

18. The composition according to claim 17 which is packaged for nasal administration.

19. The composition according to claim 18 wherein the glycyrrhizinate is present in an amount corresponding to approximately 2 g per 100 ml of composition.

20. The method of enhancing the absorption of a calcitonin across a mucosal membrane which method comprises co-administering with the calcitonin an effective amount of an absorption enhancer which is a glycyrrhizinate.

21. A liquid pharmaceutical composition comprising, as a carrier, an aqueous saline solution buffered to approximately pH 6; a non-toxic effective amount of a preservative; and, per 100ml of composition, 20,000–100,000 International Units of elcatonin and approximately 2 g of ammonium glycyrrhizinate.

22. The composition according to claim 21 packaged for administration as a spray.

* * * * *